United States Patent [19]

de Loos-Vollebregt

[11] Patent Number: 4,981,356
[45] Date of Patent: Jan. 1, 1991

[54] METHOD AND APPARATUS FOR ELECTROTHERMAL ATOMIZATION OF SAMPLES

[75] Inventor: Margaretha T. C. de Loos-Vollebregt, Nobellaan, Netherlands

[73] Assignee: The Perkin Elmer Corporation, Norwalk, Conn.

[21] Appl. No.: 400,292

[22] Filed: Aug. 29, 1989

[30] Foreign Application Priority Data

Sep. 2, 1988 [EP] European Pat. Off. ........ 88114360.6

[51] Int. Cl.⁵ ............................................. G01N 21/74
[52] U.S. Cl. ...................................... 356/312; 356/36; 356/244
[58] Field of Search ........................... 356/36, 312, 244

[56] References Cited

U.S. PATENT DOCUMENTS

| | | | |
|---|---|---|---|
| 3,982,834 | 9/1976 | Tamm | 356/244 |
| 4,111,563 | 9/1978 | Tamm | 356/312 |
| 4,147,434 | 4/1979 | Huber | 356/36 |
| 4,303,339 | 12/1981 | Glaser et al. | 356/312 |
| 4,361,401 | 11/1982 | Smith, Jr. et al. | 356/36 |
| 4,895,443 | 1/1990 | de Loos-Vollebregt et al. | 356/312 |

FOREIGN PATENT DOCUMENTS 1623062 12/1970 Fed. Rep. of Germany .
2106165 4/1983 United Kingdom .

OTHER PUBLICATIONS

Analytical Instrumentation, vol. 16, No. 2, 1987, pp. 275–280.
Article in Spectrochimica Acta, vol. 33B, 1978, pp. 153–159, "Electrothermal Atomization-The Way Toward Absolute Methods of Atomic Absorption Analysis".
Analytical Chemistry, vol. 54, No. 14, Dec. 1982, pp. 1515A–1516A and 1518A and 1520 A and 1522A and 1524A.
Trends in Analytical Chemistry, vol. 6, No. 7, Aug. 1987, pp. 171–175.
Analytical Chemistry, vol. 55, No. 2, Feb. 1983, pp. 204–208.

Primary Examiner—F. L. Evans
Attorney, Agent, or Firm—Thomas P. Murphy; Edwin T. Grimes

[57] ABSTRACT

Sample liquid is vaporized by a thermospray vaporizer with a heated capillary tube. The end of the capillary tube is inserted into a graphite tube furnace while the furnace and a vertical sample platform in the furnace is at an above-ambient deposition temperature. Vapor spray emerging from the capillary tube is directed at the platform. Sample substances are deposited on the platform while vaporized solvent is drawn off by a vacuum.

12 Claims, 6 Drawing Sheets

METHOD AND APPARATUS FOR ELECTROTHERMAL ATOMIZATION OF SAMPLES

FIELD OF THE INVENTION

This invention relates to a method and apparatus for electrothermal atomization of samples for spectrophotometric analysis, particularly analysis by means of atomic absorption spectrophotometry.

BACKGROUND OF THE INVENTION

Atomic absorption spectrophotometry (AAS) is a well-known technique for quantitative determination of an analyte element in a liquid sample. AAS makes use of the fact that atoms of an element absorb radiation in spectral lines of the same frequency as emitted by the element when subjected to appropriate stimulus. Accordingly, a beam of radiation containing the frequency absorbed by the element sought to be determined is passed through a sample and the degree of attenuation of the beam measured by a suitable detector which generates an electrical signal representative of absorption of the beam by the sample which is, at least theoretically, a function of the concentration of the analyte.

The application of this phenomenon of course requires that the sample be in atomic form. While atomization can be accomplished by directing a nebulized quantity of the liquid sample into the flame of a specially designed burner, the present invention is concerned with electrothermal or "flameless" atomizing methods and apparatus. Conventionally, electrothermal atomization employs an electric furnace consisting primarily of a graphite tube having a sample port in its side wall at the midpoint of its length. The furnace tube is mounted between electrodes engaging its ends. The electrodes are annular in form in order to accommodate passage of the spectral radiation beam emitted from a suitable source such as a hollow cathode lamp (HLC) or electrodeless discharge lamp (EDL).

The furnace tube is heated by passing an electric current longitudinally therethrough between the annular electrodes. The customary analytical procedure consists of introducing a small quantity of the liquid sample into the tube by way of the sample port and applying a relatively low current sufficient to heat the tube to a temperature sufficient to volatilize the solvent components, i.e., the drying temperature. The vaporized substances are carried off by means of a flow of inert gas through the tube. The electric current is then increased to the ashing stage, producing a temperature to cause chemical decomposition of the sample. Finally, the heating current is raised to an intensity such as to achieve a temperature effective to atomize the sample, producing a "cloud of atoms" in the furnace tube.

It is desirable to delay the atomization of the sample until the entire inner wall surface of the furnace tube attains atomization temperature. To this end, a small, essentially planar graphite member, known as a "sample platform", is placed in the tube at the sample introduction site. The platform is constructed and arranged so that conduction heating is minimized and the platform is heated substantially entirely by radiation from the walls of the tube.

The sample is introduced through the sample port and deposited on the platform. This arrangement causes a time lag in the heating of the platform delaying the volatilization and vaporization of the sample until the tube and the gasses have reached temperature equilibrium. A reduction in interferences is achieved by means of the platform furnace; however, the quantity of sample which a platform small enough to yield the benefits sought is quite limited. Larger samples are advantageous as the result in higher sensitivity.

For additional details regarding the platform furnace reference may be had to *Spectrochimica Acta*, Vol. 33B, 1978, pp. 153-159; DE-C2-29 24 123.

A recent development in the field of the invention is a method and apparatus for atomizing a sample wherein a "thermospray" vaporizing device is used. A carrier liquid such as de-ionized water is pumped through a heated capillary tube made of fused silica. The capillary tube is encased in a stainless steel tube and is axially displaceable. The stainless steel tube is heated by passing through it a high intensity electric current. Concomitantly the stainless steel tube heats the silica capillary. In its passage through the tube, the carrier liquid is at least partially vaporized and emerges from the outlet end of the tube in the form of a vapor spray.

The flow path of the liquid carrier includes, upstream of the capillary, a loop containing the sample and an injection valve operative selectively to bypass or include the loop in the flow path. When the loop is coupled in the flow path, the sample is entrained by the carrier liquid and passed through the capillary tube.

The axially displaceable tube has a first, retracted limit position and a second advanced limit position. In the advanced position the outlet end of the capillary tube extends into a graphite furnace tube of the type described above through the lateral sample introduction port in its side wall. The jet emerging from the capillary tube is directed to impinge on the inner wall of the furnace tube opposite the sample port.

In the retracted position, the outlet end of the capillary tube is disposed within a vacuum exhaust chamber, from which the spray emerging from the capillary tube is exhausted. A timer synchronizes the coupling of the sampling loop into the carrier liquid flow path and the movement of the outlet end of the capillary tube into the furnace. Thus, the capillary tube is initially in its retracted, position and water spray, issuing from the outlet end of the heated capillary tube is exhausted through the vacuum chamber. The loop is then coupled into the carrier liquid flow path by operation of the sample injection valve; the sample is entrained by the carrier liquid, carried through the capillary, and vaporized. Contemporaneously the outlet end is moved into the furnace, which is maintained at the relatively low drying temperature. The sample components of interest are deposited on the inner wall of the furnace tube while the vehicle and solvent vapor is removed by flow of inert gas through the furnace.

The furnace is then heated to atomizing temperature and the absorption of the beam of radiation by the cloud of atoms is measured as previously explained. As there is no need to accommodate all of the solvent within the furnace, much larger sample quantities can be used so that the sensitivity of the measurement is enhanced. Moreover, inasmuch as the furnace need not be cooled down to ambient temperature after each analysis but remains at the elevated level of the drying temperature, the analytical cycle time is reduced considerably. During the heating of the furnace to atomizing temperature, a shield is inserted between the vacuum exhaust chamber and the furnace in order to protect the hot furnace from the spray emerging from the capillary tube.

SUMMARY OF THE INVENTION

It is the basic, general object of the invention to provide a method and apparatus for electrothermal atomization of a sample which permits atomization of relatively large quantities of sample within a short time interval in order to achieve high spectrophotometric sensitivity.

To the fulfillment of this object and others which will become apparent as this description proceeds, the invention contemplates a method which comprises heating to an above-ambient temperature a hollow furnace member having a sample platform therein disposed and arranged to be heated primarily by radiation from the inner walls of the furnace and having a surface adapted to receive a sample. A liquid sample is heated in a capillary tube so as to cause at least a major portion to vaporize. One end of the tube is intermittently inserted into the furnace and forms a jet of the vaporized sample injected into the furnace substantially normal to, and impinging on, the platform surface so that a portion of the vaporized sample is deposited on the platform. Another portion of the sample, not deposited on the platform, is removed and the furnace heated to a temperature higher than the first temperature and sufficient to atomize the sample portion deposited on the platform surface. The atomized sample is then spectrophotometrically analyzed and the furnace allowed to cool to the first temperature.

The apparatus contemplated by the invention for fulfillment of its objects comprises a hollow furnace member having a side wall containing a sample introduction port and defining a path for passage of a radiation beam through the member. A sample platform disposed opposite the sample port is arranged to be heated indirectly by radiation from the inner walls of the furnace and having a surface configured and adapted to receive a sample. Means are provided for passing an electric current through the furnace member to maintain the member at a first above ambient temperature and for passing a higher current to heat the furnace member to a temperature sufficient to atomize a sample on the sample receiving surface of the platform. Means are also provided for spectrophotometric analysis of the sample comprising a heated capillary tube having an outlet end and means for passing a liquid sample through the heated capillary tube to vaporize at least a major portion of said sample and to provide a jet of vaporized sample emerging from the outlet end. Means are also provided for intermittently inserting the outlet end of the capillary axially through the sample port into the cavity of the furnace. The sample port is located opposite the sample-receiving surface of the platform and the sample receiving surface is substantially perpendicular to the capillary tube; consequently the jet impinges on the sample-receiving surface and a portion of the vaporized sample is deposited thereon. Means, operative during the subsistence of the first temperature, are provided for removing from the furnace portions of the vaporized sample not deposited on the platform. Timer means control the flow of sample liquid through the heated capillary; for inserting the outlet end of the capillary tube into the furnace cavity; for operation of the vapor-removing means; and for regulation of the heating current governing the duration of the first and second temperature so as to cause the sample to be passed through the capillary tube, the capillary tube to be inserted into the furnace cavity and the non-deposited portion of the sample vapor to be removed during the subsistence of the first temperature and the capillary to be removed during the subsistence of the second temperature The invention uses an indirectly heated sample platform, thus ensuring that all of the sample is vaporized within a short time interval, when the furnace wall has already been heated to atomization temperature. By use of the thermospray for depositing the sample on the platform, eliminating the solvent by vaporization, it becomes possible to use the platform with rather large quantities of sample. Preferably the step of removing the non-deposited portion of the sample is accomplished by establishing communication between the furnace and a source of vacuum.

An embodiment of the invention is described hereinbelow with continued reference to the accompanying drawings.

BRIEF DESCRIPTION OF THE DRAWINGS

FIG. 5 is a cross-sectional view of a graphite tube furnace with a sample platform on which sample vapor is deposited by the thermospray device.

PREFERRED EMBODIMENT OF THE INVENTION

Figure 1:
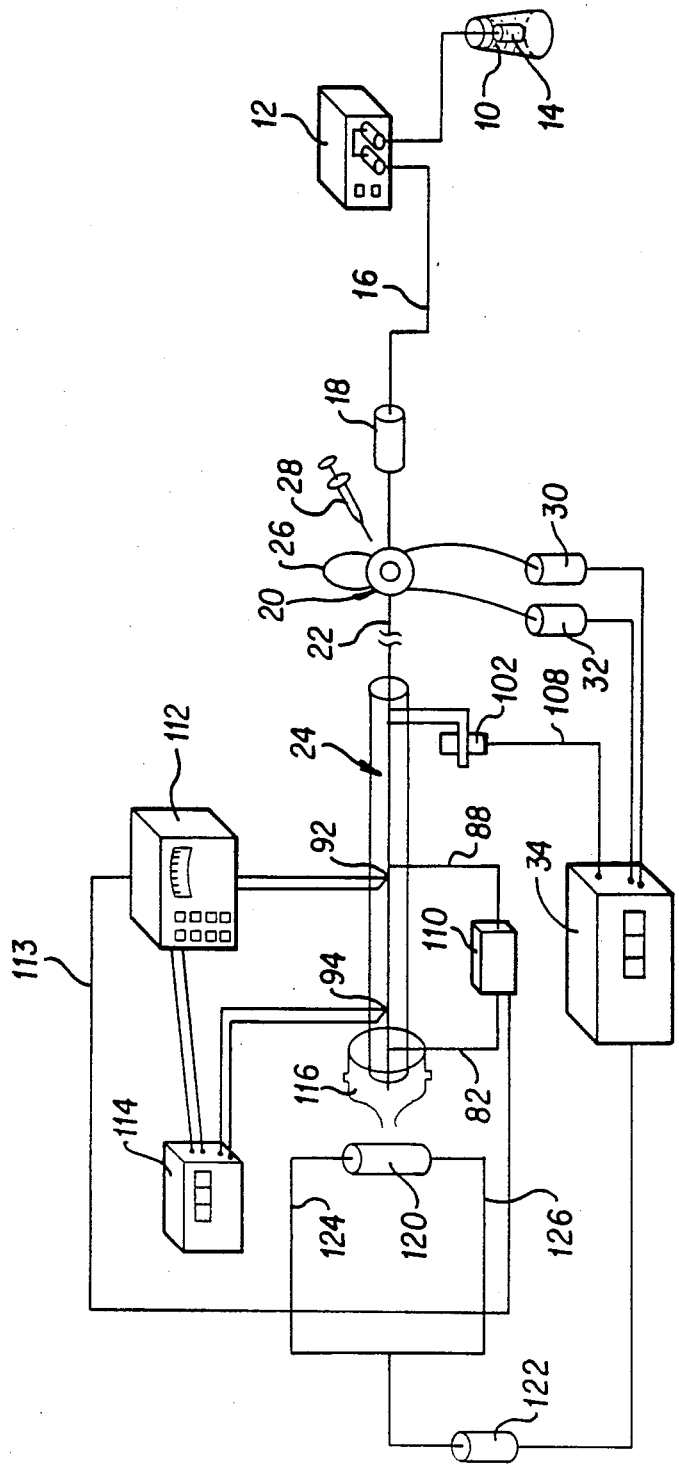
FIG. 1 is a diagrammatic representation of an apparatus for electrothermal atomization of samples for spectrophotometric analysis.

Referring to the drawings and first in particular to FIG. 1, numeral 10 designates a vessel containing deionized water. A high pressure pump 12, similar to those used in high pressure liquid chromatography (HPLC) but constructed entirely of plastics to ensure that no metal ions from pump components enter the water, aspirates water from vessel 10 through a filter 14. The water is pumped through a conduit 16 and a cation exchange column 18 to an injection valve 20, also of the type used in HPLC, i.e., using the flow injection technique.

In a first setting, valve 20 connects conduit 16 directly with a conduit 22 leading to a thermospray vaporizer 24; in a second setting, the valve connects conduit 16 with an inlet end of a sample loop 26 and connects the outlet end of the sample loop to conduit 22. Thus, in the second valve position, water from pump 12 is passed through sample loop 26 entraining a sample which may be deposited therein as by means of a syringe 28. Valve 12 is actuated pneumatically through pneumatic valves 30 and 32 which, in turn are controlled by a timer 34, as will be seen as this description proceeds.

Figure 4:
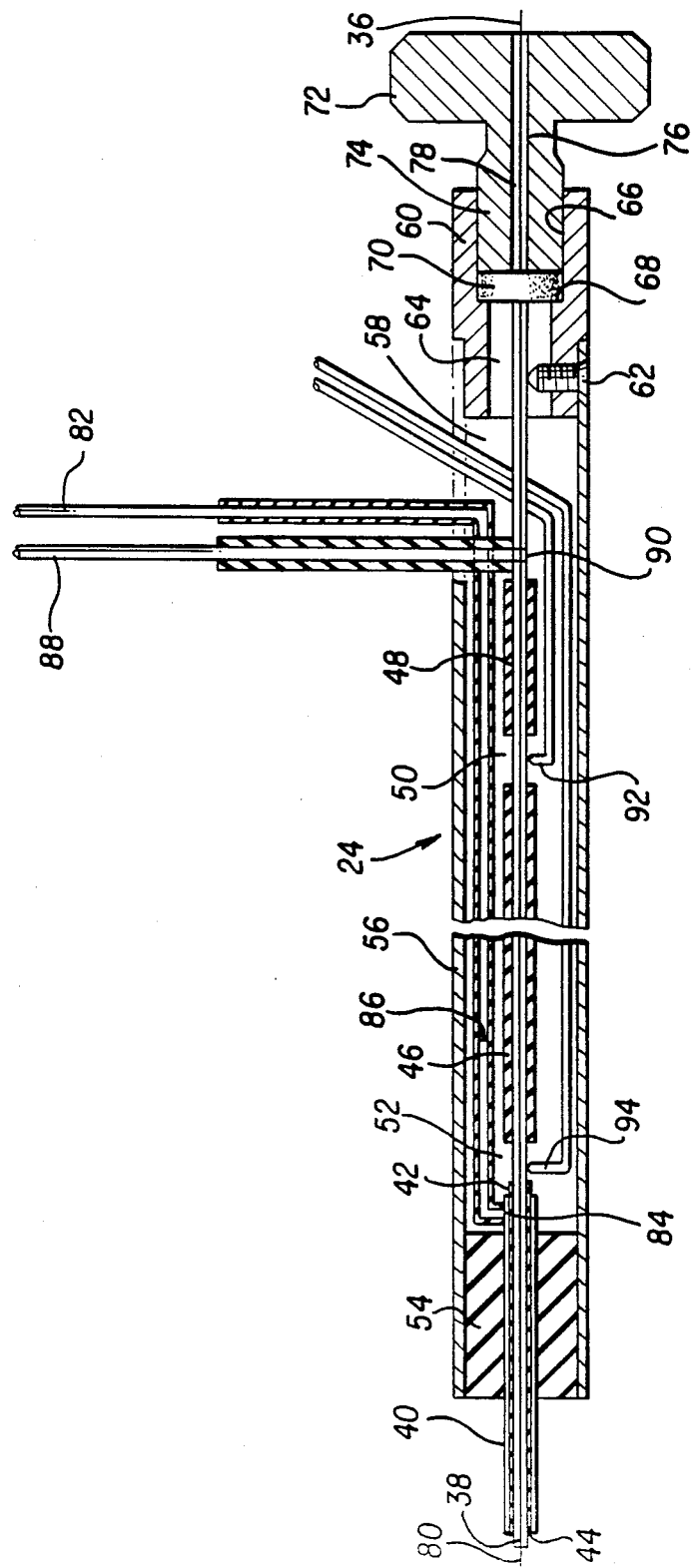
FIG. 4 is a longitudinal sectional view of the thermospray device.

Thermospray vaporizer 24, illustrated in greater detail in FIG. 4, comprises a capillary tube 36 of fused silica which is connected to conduit 22 or, if desired, may be a section of the capillary tube. A stainless steel tube 38 coaxially encases capillary tube 36. A length 40 of stainless steel tube, shorter than tube 38 but of larger diameter, coaxially surrounds a section of tube 38 adjacent its left hand end as viewed in FIG. 4. Steel tubes 38 and 40 are electrically insulated from each other over most of their joint length by a glass layer 42 but are electrically connected at the left end 44.

Intermediate its ends, steel tube 38 is coaxially enveloped by a length of insulating glass tube 46 and by an insulating glass tube 48 to the right of and axially spaced from tube 46 as indicated at 50. The left end of tube 46 is similarly axially separated from steel tube 40 by a space 52. A bushing 54 of electrically insulative material coaxially supports the left hand end of the tube assembly in a relatively large diameter outer tube 56, preferably of stainless steel.

At its right hand end, outer tube 56 carries a generally tubular collar 60 secured thereto be means of a set screw 62. Collar 60 contains a bore 64 and a counterbore 66 of larger diameter than bore 64 so as to form at their junction a shoulder 68 providing a seat for a silicon rubber disk 70. A removable bushing member 72 has a shaft portion 74 which is a push fit in counterbore 66, the inner end of which abuts disk 70. The right hand end 78 of capillary tube 36, together with its encasing steel tube 38, extends through disk 70 and a bore 76 in bushing member 72, thus supporting the tube assembly coaxially with outer tube 56.

At the opposite end of the tube assembly, supported in bushing 54, a tip 80 of the capillary tube 36 projects about two millimeters beyond the encasing steel tube 38.

An axial slot 58 in outer tube 56 adjacent its right hand end accommodates the passage of an electrical conductors 82 and 88. Conductor 82 extends through the tube along glass tube 46 to steel tube 40 to which it is electrically connected at 84. Conductor 82 is made of copper up to the junction 86 and beyond that point of stainless steel. A return conductor 88 is electrically connected to steel tube 38 at 90.

Respective thermocouples 92 and 94 extend through spaces 50 and 52 and contact steel tube 38 at axially spaced points so as to continuously measure the temperature of the tube a locations near the inlet and outlet of thermospray vaporizer 24.

Figure 2:
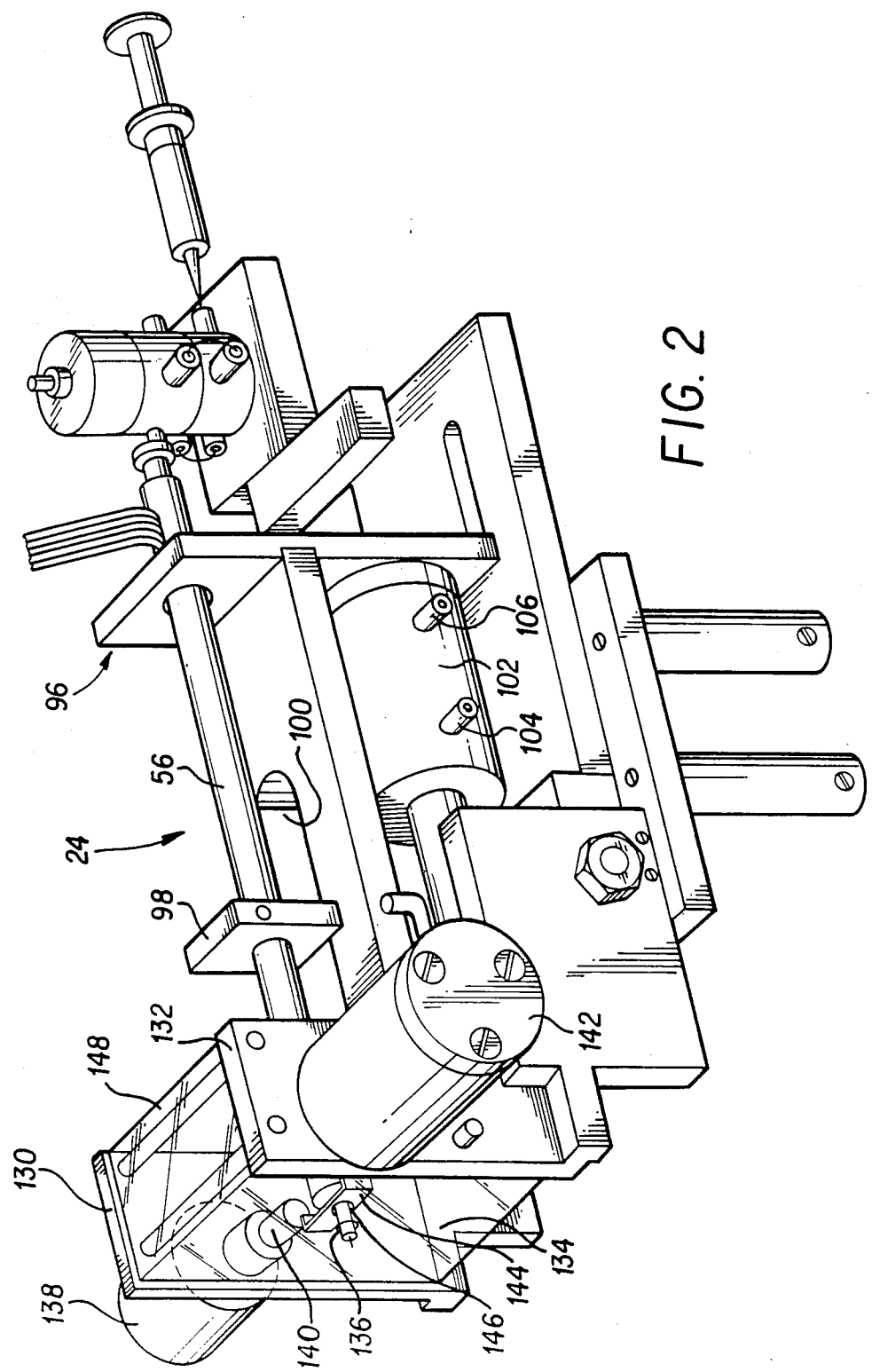
FIG. 2 is a perspective view of the thermospray device in the FIG. 1 apparatus.
Figure 3:
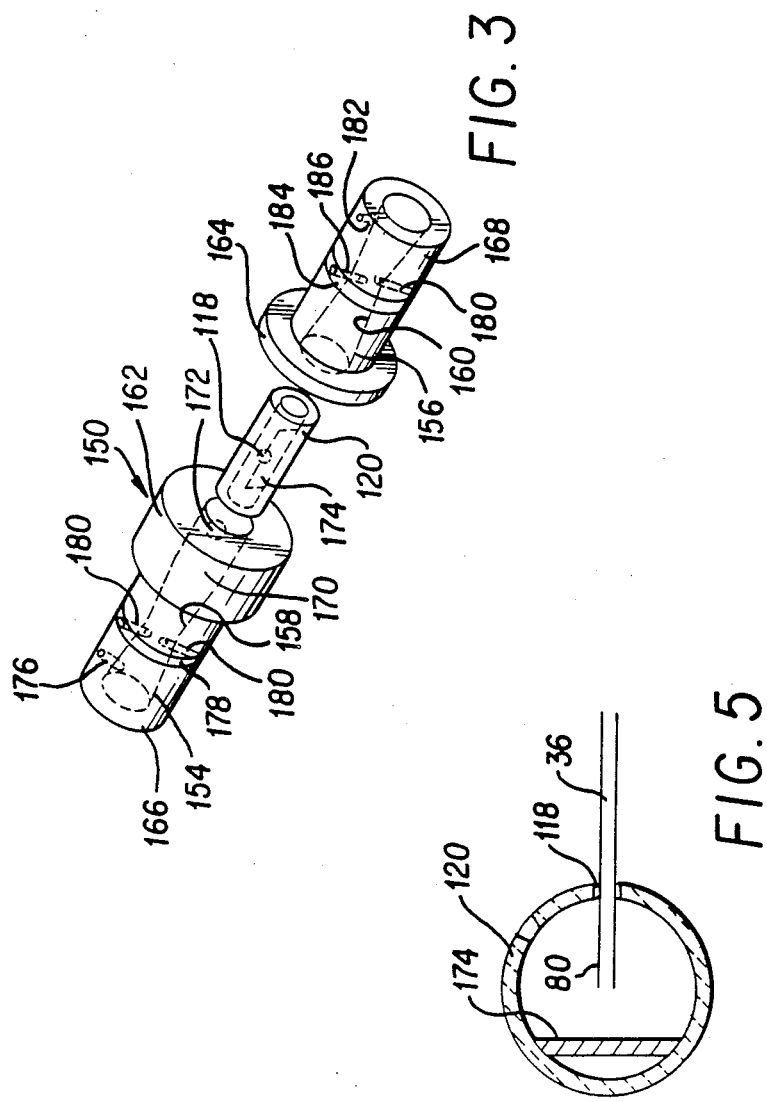
FIG. 3 is an exploded, perspective view of a portion of FIGS. 1 and 2, viz., the electrode members mounting the furnace and the inert gas and vacuum passages.

The entire tube assembly shown in FIG. 4, consisting of capillary 36 steel tubes 38 and 40, glass tubes 46 and 48 and outer tube 56 is mounted for axial displacement in a vaporizer base structure 96 as best appears in FIG. 2. To this end a carriage 98 is secured to outer tube 56 and is guided in a slot 100 in the base structure. Carriage 98 is mechanically coupled to a pneumatic actuator 102 which includes a cylinder (not shown) and a double-acting piston (also not shown) reciprocatably disposed therein.

The working cylinder chambers defined within actuator 102 are in flow communication with conduits 104 and 106 to and from which the pneumatic working medium is supplied and exhausted under control of a timer 34 as indicated by line 108 in FIG. 1. Thus, the actuator is arranged to axially displace outer tube 56 and jointly therewith the remainder of the tube assembly, including the capillary tube 36, between first and second limit positions as will be described presently.

Slot 58 in tube 56 accommodates the displacement while providing for passage of conductors 82 and 88 which are connected to a transformer 110 to provide a high current of about 20 amperes through steel tube 38. The current flows through conductor 82, steel tube 40 (FIG. 4), and from the end 44 of tube 40 (and virtually the end of steel tube 38) through tube 38 to return conductor 88. In this manner, Joule's heating of steel tube 38 and, concomitantly, capillary 36, is effected nearly up to its forward end. Consequently, there is no condensation or heat dissipation from the sample vapor emerging, in operation, from the forward end of capillary tube 36.

The temperature signal from thermocouple 92 is applied to a temperature controller 112 which regulates current through transformer 110 as indicated by line 113 to maintain a desired temperature of, for example, 300 degrees C. in tube 38. The temperature signal from thermocouple 94, which represents the temperature of steel tube 38 and capillary tube 36 near the tip 80, is applied to a temperature display device 114 from which the actual temperature can be read.

In its retracted position, as shown in FIG. 1, the outlet end of capillary tube 36 is disposed with a vacuum exhaust chamber 116 connected to a vacuum source (not shown). In its forward limit position, the tip 80 of the capillary tube extends through a sample introduction port 118 into a graphite tube furnace member 120 (FIG. 5). Furnace member 120 in connected through conduits 124,126 to a furnace vacuum system 122 which is also controlled by timer 34 as indicated by line 128 (FIG. 1).

Reverting to FIG. 2, a shield is provided between the furnace and the furnace exhaust chamber 116. The shield, which is not shown in FIG. 1 to simplify the illustration, comprises two vertical side plates 130,132 interconnected by front plate 134 and top plate 148. Side plates 130,132 are secured to the base structure on opposite sides of the outer tube 56 of the thermospray device 24. Front plate 134 contains an aperture 136 coaxially aligned with the capillary tube 36.

A pneumatic actuator 138, mounted on side plate 130, is aligned with a similar actuator 142 on side plate 132; each has a piston rod albeit only that of actuator 138 is visible (at 140). The piston rods are aligned but oppositely directed and have a shield member or shutter plate 144 mounted between them. Shutter plate 144 contains an aperture 146 which is in alignment with hole 136 in front plate 134 in one of the limit positions of the actuators. Thus, when actuator 138 is supplied with gas under pressure shutter member 144 is shifted to a position in which aperture 146 is out of alignment with aperture 136 in front plate 134. Consequently, aperture 136 is occluded by the shutter plate and the furnace shielded from exposure to vapor issuing from the end of capillary tube 36. When actuator 142 is activated (i.e., pressurized) the action is reversed: aperture 136 and 146 are aligned and tip 80 of capillary tube 36 is able to move to its forward limit position with tip 80 inserted into sample introduction port 118.

Graphite furnace tube 120 is disposed between electrode members 150 and 152 which provide both mechanical support for, and electrical connections to, the tube. Electrodes 150 and 152 contain respective through bores or passages 154,156 and each comprises a head portion 162, 164 and shaft portion 166, 168 respectively. The head 162 of electrode member 150 contains a cavity 170 coaxial with respect to bore 154 and configured to substantially completely envelope furnace tube 120. The head portion 164 of electrode member 152 is discoid in configuration and closes the cavity 170 except for a narrow gap between the electrodes 150,152. Bores 154 and 156 taper inwardly in a direction away from cavity 170 and to provide annular contact surfaces 158, 160 for the respective ends of graphite furnace tube 120.

Head portion 162 of electrode 150 contains a lateral bore 172 which is aligned with the sample introduction port 118 when tube 120 is inserted into the cavity 172 and electrodes 150,152 are assembled in operative relation. Moreover, in such operative relation, the axes of bore 172 and port 118 are aligned with the axis of capillary tube 36.

Graphite tube 120 contains a sample platform 174 consisting of a small planar piece of graphite having a sample receiving surface disposed in a chordal plane directly opposite sample port 118 and perpendicular to the axis of the capillary tube 36. The platform is dimensioned and arranged within the furnace in a manner calculated to minimize direct heating by conduction or the Joule's effect. On the contrary heating of the platform is primarily by way of radiation form the wall of the furnace member 120.

Electrode 150 contains a vacuum passage 176 through which the longitudinal bore 154 may be connected to vacuum system 122 through passage 126 (FIG. 1). In addition, shaft 166 of electrode member 150 contains an annular groove 178 in its outer circumferential surface arranged to be connected to a source of inert gas. Electrode member 150 contains inert gas passages 180 connecting annular groove 178 with longitudinal bore 154.

Similarly, contact 152 contains a vacuum passage 182 through which longitudinal bore 156 is connected to vacuum system 122 through passage 126. Shaft portion 168 of electrode 152 has an annular groove 184 in its outer circumferential surface arranged to be connected to a source of inert gas. Electrode 152 contains inert gas passages 186 which connect annular groove 184 with longitudinal bore 156.

Operation

At the outset of operation, valve 20 is placed in a position in which the flow of water from pump 12 is fed directly into conduit 22 and capillary tube 36, bypassing loop 26. Steel tube 38 is heated by current from transformer 110. At this stage, actuator 102 has moved outer tube 56 together with capillary tube 36 and the remainder of the tube assembly as a unit into the retracted position. Consequently, tip 80 of the capillary tube is disposed in vacuum exhaust chamber 116 and water, vaporized in capillary tube 36 and issuing from its forward end as vapor or spray, is exhausted through the vacuum exhaust chamber. At this time actuator 138 may be energized to move the shutter member 144 so that apertures 136 and 146 are out of registration and the furnace tube 120 is shielded from any water vapor which might emerge from the vacuum exhaust chamber. Also during this time, furnace tube 120 is maintained at a relatively low (deposition) temperature.

With the system in this condition a liquid sample containing sample elements is introduced into sample loop 26 by means of a syringe 28. Timer 34 then actuates the sample injection valve so that it is coupled in the flow path of water from pump 12 to vaporizer 24. Thus the sample is entrained in the carrier water and transported to the vaporizer. Contemporaneously timer 34 activates pneumatic actuator 142 to move shutter plate 144 so as to bring aperture 146 into registration with aperture 136. Subsequently, timer 34 activates pneumatic actuator 102 to move with outer tube 56 the enclosed tube assembly to its forward limit position. In this position, the forward ends of steel tubes 38,40 and capillary tube 36 extend through apertures 136 and 146. The tip 80 of capillary tube 36 extends through the sample port 118 into furnace member 120, as illustrated in FIG. 5. At the same time, timer 34 initiates operation of vacuum system 122.

Sample liquid vaporized in thermospray device 24 emerges as a jet of vapor directed against platform 174 which, like the remainder of furnace 120, is at relatively low but above ambient deposition temperature. Solvent vapor, therefore, does not condense on platform 174 nor anywhere else within furnace 120. This solvent vapor is exhausted by the vacuum system through vacuum passages 180, 186. Due to removal of vaporized solvent, only the elements of the sample proper are deposited on the platform. This makes it possible for small platforms to accommodate relatively large samples, e.g., 20 to 80 microliters.

After sample deposition, operation of actuator 102 is initiated by timer 34 to restore the vaporizer tube assembly to its retracted limit position and actuator 138 is energized to restore shutter plate 144 to its position of occlusion of aperture 136 to shield furnace 120. This done, the furnace is heated to atomization temperature. When the inner walls of the furnace have reached atomization temperature, the platform and the sample deposited thereon are heated to this temperature, mainly by radiation, and the sample atomized.

After spectroscopic measurement, current to furnace 120 is switched off enabling the furnace to cool down to the above-ambient deposition temperature. When this temperature has been reached, the electric heating current is re-applied, at a lower value required to maintain the furnace at deposition temperature.

Figure 6:
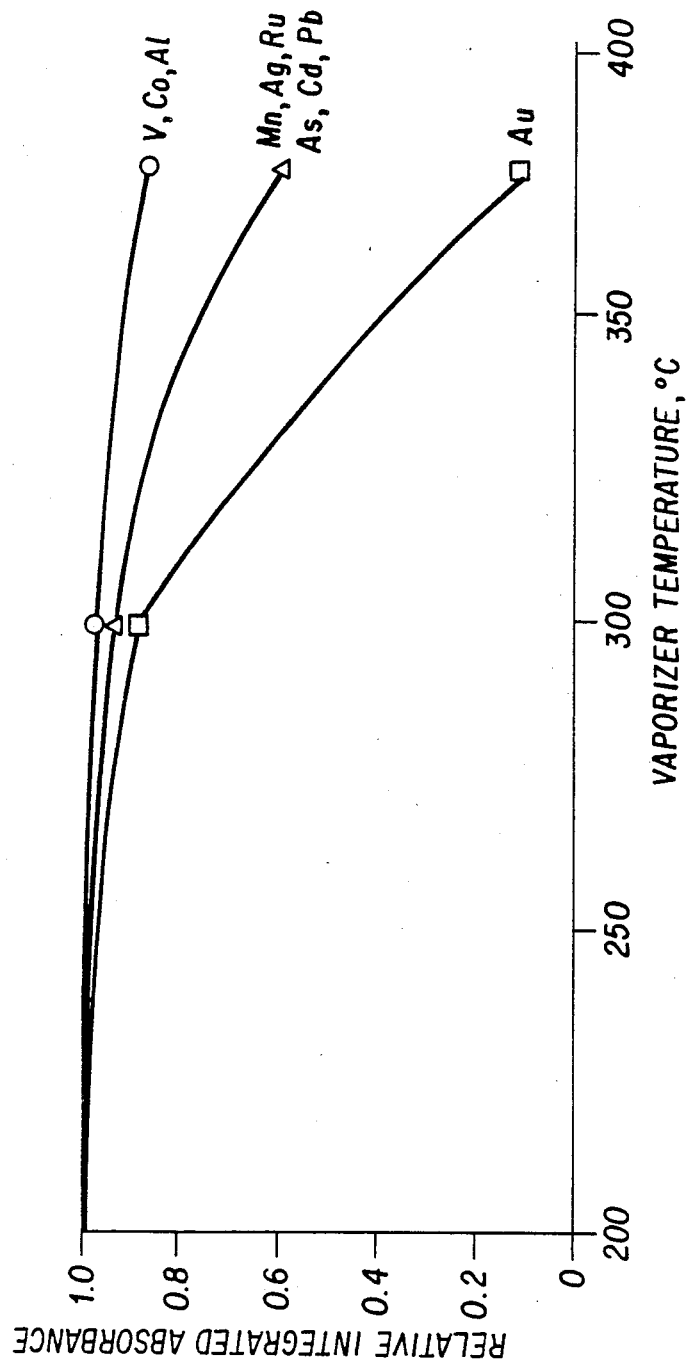
FIG. 6 is a graph plotting the relative integrated absorbance as a function of the vaporizer temperature for a number of elements.
Figure 7:
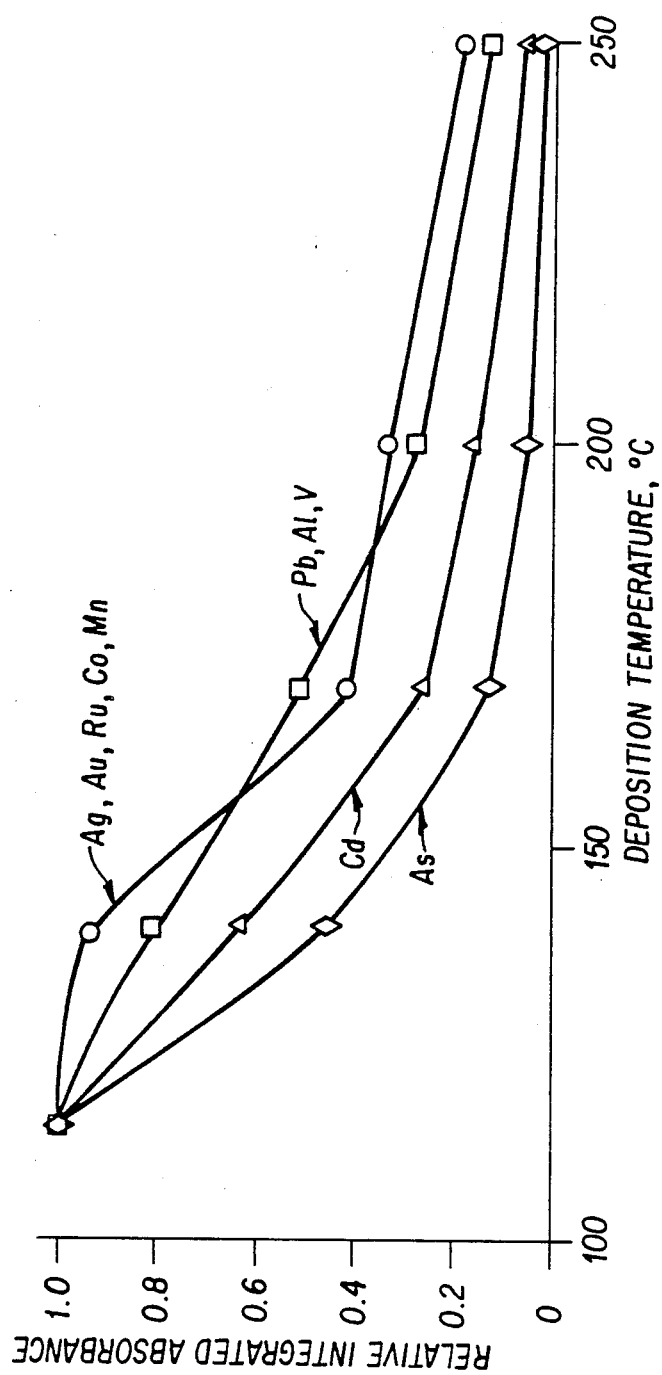
FIG. 7 is a graph plotting the relative integrated absorbance vs. deposition temperature, i.e., the temperature of the walls of the furnace when the sample is deposited by the thermospray vaporizer.

FIG. 6 shows the relative integrated absorbance obtained for different elements with different vaporizer temperatures (measured by thermocouple 94). The absorbance remains essentially constant up to a vaporizer temperature of 300 degrees C. and then starts to drop. Thus a temperature of about 300 degrees C. appears to be optimum. It provides a dry spray at the outlet of the capillary tube 36 while maintaining high efficiency. From FIG. 6 it will be noted that absorbance drops sharply at deposition temperatures above 170 degrees C. Such a temperature appears to be optimum, because it safely prevents condensation of the solvent and reduces the time required for the cooling down of the furnace, without loss of efficiency.

The apparatus and method described offer a number of advantages: the high efficiency of the platform technique, due primarily to the fact that the sample is vaporized with delay but substantially instantaneously, can be utilized without the customary limitations on sample size. Moreover, as the entire tube assembly is displaced as a unit, the fine capillary tube can be supported practically up to the tip 80. Consequently the position of the tip is well-defined, permitting reduction in the diameter of the sample port of the furnace, particularly when compared with ports in furnaces intended for use with conventional pipette sample introduction techniques. The reduction in sample port diameter reduces the rate at which atomic vapor formed within the furnace is flushed out of the furnace through the introduction port by inert gas flowing inwardly from the ends of the furnace tube. The selection of the temperatures reduces the proportion of liquid solvent in the emerging vapor and consequently the quantity of such liquid solvent which can be deposited on the platform.

What is claimed is:

1. A method for electrothermal atomization of samples for spectrophotometric analysis comprising the steps of:
   (a) heating, to a first above-ambient temperature, a hollow furnace member having a sample platform therein constructed and arranged to be heated primarily by radiation from the inner walls of said member and having a surface configured to receive a sample;
   (b) heating a liquid sample in a capillary tube so as to vaporize at least a portion thereof;
   (c) intermittently inserting one end of the tube into said furnace and forming a jet of the vaporized sample directed substantially normal to said platform surface so as to impinge thereon, whereby a portion of the sample is deposited thereon;
   (d) removing another portion of the vaporized sample not deposited on said platform, said step comprising establishing communication between said furnace and a vacuum source;
   (e) heating the furnace to a temperature higher than said first temperature and sufficient to atomize said sample portion deposited on said platform surface;
   (f) spectrophotometrically analyzing said atomized sample; and
   (g) allowing the furnace to cool down to said first temperature.

2. A method as defined in claim 1 wherein said platform is arranged with said sample receiving surface substantially vertical and said tube is substantially horizontal and axially displaceable.

3. A method as defined in claim 1 wherein the tube is heated to a temperature in excess of 250 degrees C.

4. A method as defined in claim 3 wherein said tube is heated to a temperature of about 300 degrees C.

5. An apparatus for electrothermal atomization of samples for spectrophotometric analysis, comprising:
   (a) a hollow furnace member having a sidewall containing a sample introduction port;
   (b) a platform member disposed within said hollow member constructed and arranged to be heated primarily by radiation from the inner surface of said sidewall and having a surface in apposition to said port and configured to receive a sample;
   (c) means for passing an electric current through said furnace member to heat it to a first above ambient temperature and for subsequently passing a higher electric current to heat the furnace member to a second, higher temperature sufficient to atomize a sample on the sample receiving surface of said platform;
   (d) a heated capillary tube;
   (e) means for passing a liquid sample through said heated capillary tube to vaporize therein at least a major portion of said sample and to form a jet of vaporized sample emerging from one end of the tube;
   (f) means for intermittently axially displacing said tube to a position in which said one end projects through said port into said furnace member along a line substantially normal to the sample receiving surface whereby said jet impinges and deposits a portion of said vaporized sample thereon;
   (g) means operative during the subsistence of said first temperature for removing from the furnace a portion of said sample not deposited on said platform, said last named means comprising means for establishing flow communication between said furnace member and a vacuum source; and
   (h) timer means for synchronizing the axial displacement of said capillary tube, the flow of sample in said tube, the heating of said furnace member to said first and second temperatures and operation of said sample removing means so as to cause the sample to flow through the capillary tube, the one end of the tube to be inserted through said sample port into said hollow furnace member and non-deposited vapor from the tube to be removed from the furnace member during the subsistence of said first temperature, and said tube to be withdrawn from said furnace member during subsistence of said second temperature.

6. Apparatus according to claim 5 wherein said current passing means comprise a pair of electrode members providing mechanical support for said furnace member and electrical contacts for passing electrical current therethrough, and said sample removing means comprise passages in said electrode members each communicating at one end with the interior of the hollow furnace member and adapted at the other end for connection to a vacuum source.

7. Apparatus according to claim 6 wherein said furnace member is tubular in form and said electrode members coact to define a cavity receiving and substantially entirely enveloping the furnace member and having respective apertures coaxially aligned with the ends of said tubular furnace member to permit passage of a beam of spectral radiation.

8. Apparatus according to claim 7 wherein said electrode members contain respective through bores coaxially aligned with said apertures and said vapor-removing passages open into said bores.

9. Apparatus according to claim 5 wherein said capillary tube extends substantially horizontally and said sample receiving surface is substantially normal thereto.

10. An apparatus for electrothermal atomization of samples for spectrophotometric analysis, comprising;
   (a) a hollow furnace member having a sidewall containing a sample introduction port;
   (b) a platform member disposed within said hollow member constructed and arranged to be heated primarily by radiation from the inner surface of said sidewall and having a surface in apposition to said port and configured to receive a sample;
   (c) means for passing an electric current through said furnace member to heat it to a first above ambient temperature and for subsequently passing a higher electric current to heat the furnace member to a second, higher temperature sufficient to atomize a sample on the sample receiving surface of said platform;
   (d) a heated capillary tube;
   (e) means for passing a liquid sample through said heated capillary tube to vaporize therein at least a major portion of said sample and to form a jet of vaporized sample emerging from one end of the tube;
   (f) means for intermittently axially displacing said tube to a position in which said one end projects through said port into said furnace member along a line substantially normal to the sample receiving surface whereby said jet impinges and deposits a portion of said vaporized sample thereon;

(g) means operative during the subsistence of said first temperature for removing from the furnace a portion of said sample not deposited on said platform;

(h) timer means for synchronizing the axial displacement of said capillary tube, the flow of sample in said tube, the heating of said furnace member to said first and second temperatures and operation of said sample removing means so as to cause the sample to flow through the capillary tube, the one end of the tube to be inserted through said sample port into said hollow furnace member and non-deposited vapor from the tube to be removed from the furnace member during the subsistence of said first temperature, and said tube to be withdrawn from said furnace member during subsistence of said temperature;

(i) an electrically conductive tube coaxially surrounding said capillary tube;

(j) means connecting spaced points of said electrically conductive tube to an electric power source for passing an electric current through and directly heating the conductive tube with concomitant heating of the capillary tube; and (k) means for mounting said capillary tube and electrically conductive tube for joint axial displacement between a first limit position in which said outlet end extends through the sample introduction port into the furnace member and a second limit position in which said outlet end is withdrawn from the sample introduction port; and (l) means for moving said capillary and conductive tubes conjointly between said first and second limit positions.

11. Apparatus according to claim 10 further comprising:

(a) a second electrically conductive tube shorter in length and larger in diameter than the first mentioned conductive tube coaxially surrounding, said second tube surrounding a section of the first conductive tube adjacent the outlet end of the capillary tube;

(b) an insulating layer interposed between said first and second conductive tubes; and (c) means electrically connecting said electrically conductive tubes at the ends adjacent said outlet end, a contact for passing current through the first electrically conductive tube being electrically connected to the second electrically conductive tube proximate the end thereof remote from said outlet end.

12. Apparatus according to claim 10 wherein said capillary tube extends substantially horizontally and said sample receiving surface is substantially normal thereto.

* * * * *